(12) United States Patent
Wulfman et al.

(10) Patent No.: US 8,951,224 B2
(45) Date of Patent: Feb. 10, 2015

(54) INTERVENTIONAL CATHETER ASSEMBLIES, CONTROL SYSTEMS AND OPERATING METHODS

(71) Applicant: Boston Scientific Limited, Hamilton HM11 (BM)

(72) Inventors: Edward I. Wulfman, Woodinville, WA (US); Casey Torrance, Seattle, WA (US); Brian Cran, Seattle, WA (US); Scott Youmans, Bothell, WA (US)

(73) Assignee: Boston Scientific Limited, Hamilton (BM)

( * ) Notice: Subject to any disclaimer, the term of this patent is extended or adjusted under 35 U.S.C. 154(b) by 89 days.

(21) Appl. No.: 13/691,634

(22) Filed: Nov. 30, 2012

(65) Prior Publication Data

US 2013/0345676 A1    Dec. 26, 2013

Related U.S. Application Data

(62) Division of application No. 12/769,587, filed on Apr. 28, 2010, now Pat. No. 8,323,240, which is a division of application No. 10/798,621, filed on Mar. 10, 2004, now Pat. No. 7,713,231.

(60) Provisional application No. 60/453,846, filed on Mar. 10, 2003.

(51) Int. Cl.
   *A61M 37/00*    (2006.01)
   *A61M 25/01*    (2006.01)
   (Continued)

(52) U.S. Cl.
   CPC ............ *A61M 25/0147* (2013.01); *A61B 5/061* (2013.01); *A61B 5/415* (2013.01);
   (Continued)

(58) Field of Classification Search
   CPC ................ A61B 17/320758; A61B 2217/005; A61B 17/32002; A61B 17/320725; A61B 5/061; A61B 5/418; A61M 39/06; A61M 39/0606; A61M 25/0147; A61M 2039/062
   USPC ......... 604/93.01, 95.01, 95.05, 156; 606/159, 606/167
   See application file for complete search history.

(56) References Cited

U.S. PATENT DOCUMENTS

| 3,743,443 | A |   | 7/1973 | Jennings |
| 4,137,570 | A | * | 1/1979 | Baker ............................. 363/43 |

(Continued)

FOREIGN PATENT DOCUMENTS

WO            01/76680 A1    10/2001

OTHER PUBLICATIONS

Wulfman, Edward I., et al., "USPTO Office Action; Examiner Mendoza, Michael G.,"U.S. Appl. No. 10/798,601, filed Mar. 10, 2004 (Oct. 18, 2013).

*Primary Examiner* — Aarti B Berdichevsky
(74) *Attorney, Agent, or Firm* — Seager, Tufte & Wickhem, LLC

(57) ABSTRACT

An interventional catheter assembly has an operating head and catheter system that are inserted and navigated within a patient's body while an operator controls the system externally of the operating head. An operating head is positioned at or near a distal end of the catheter system and coupled to a drive shaft and drive system for rotation. A guidewire brake control system interrupt prevents the drive system from being actuated when the guidewire brake is in a released position, and a selectable guidewire brake interrupt override control permits an operator to translate and/or rotate the drive shaft and operating head while the guidewire is simultaneously moved. This allows withdrawal of the guide wire and the operating head from the target site while rotating the operating head.

19 Claims, 12 Drawing Sheets

(51) Int. Cl.
    *A61B 5/06*     (2006.01)
    *A61B 5/00*     (2006.01)
    *A61B 8/00*     (2006.01)
    *A61B 17/3207*     (2006.01)
    *A61M 39/06*     (2006.01)
    *A61B 8/12*     (2006.01)
    *A61B 17/32*     (2006.01)
    *A61B 17/34*     (2006.01)
    *A61B 17/00*     (2006.01)
    *A61B 17/22*     (2006.01)
    *A61B 17/29*     (2006.01)

(52) U.S. Cl.
    CPC ............. *A61B 5/418* (2013.01); *A61B 8/4209* (2013.01); *A61B 17/320725* (2013.01); *A61B 17/320758* (2013.01); *A61M 39/06* (2013.01); *A61B 8/12* (2013.01); *A61B 17/32002* (2013.01); *A61B 17/3462* (2013.01); *A61B 2017/00017* (2013.01); *A61B 2017/00199* (2013.01); *A61B 2017/00973* (2013.01); *A61B 2017/22049* (2013.01); *A61B 2017/2927* (2013.01); *A61B 2017/320032* (2013.01); *A61B 2217/005* (2013.01); *A61M 39/0606* (2013.01); *A61M 2039/062* (2013.01)
    USPC .................................................... 604/95.01

(56) References Cited

U.S. PATENT DOCUMENTS

| | | | |
|---|---|---|---|
| 4,445,509 A | 5/1984 | Auth | |
| 4,705,038 A * | 11/1987 | Sjostrom et al. | 606/180 |
| 4,857,045 A | 8/1989 | Rydell | |
| 5,026,384 A | 6/1991 | Farr et al. | |
| 5,100,426 A * | 3/1992 | Nixon | 606/170 |
| 5,135,483 A * | 8/1992 | Wagner et al. | 604/22 |
| 5,372,602 A | 12/1994 | Burke | |
| 5,395,311 A * | 3/1995 | Andrews | 604/22 |
| 5,527,325 A | 6/1996 | Conley et al. | |
| 5,584,843 A | 12/1996 | Wulfman et al. | |
| 5,728,129 A * | 3/1998 | Summers | 606/170 |
| 5,769,085 A | 6/1998 | Kawakami et al. | |
| 5,769,086 A | 6/1998 | Ritchart et al. | |
| 5,921,956 A * | 7/1999 | Grinberg et al. | 604/95.01 |
| 5,938,670 A | 8/1999 | Keith et al. | |
| 5,957,941 A | 9/1999 | Ream | |
| 5,972,012 A * | 10/1999 | Ream et al. | 606/170 |
| 6,001,112 A | 12/1999 | Taylor | |
| 6,080,170 A | 6/2000 | Nash et al. | |
| 6,206,898 B1 | 3/2001 | Honeycutt et al. | |
| 6,258,111 B1 | 7/2001 | Ross et al. | |
| 6,270,477 B1 | 8/2001 | Bagaoisan et al. | |
| 6,398,755 B1 * | 6/2002 | Belef et al. | 604/95.01 |
| 6,451,036 B1 | 9/2002 | Heitzmann et al. | |
| 6,565,588 B1 | 5/2003 | Clement et al. | |
| 6,599,265 B2 | 7/2003 | Bon | |
| 6,666,874 B2 | 12/2003 | Heitzmann et al. | |
| 6,726,675 B1 * | 4/2004 | Beyar | 604/510 |
| 7,172,610 B2 | 2/2007 | Heitzmann et al. | |
| 7,479,147 B2 * | 1/2009 | Honeycutt et al. | 606/159 |
| 7,674,272 B2 * | 3/2010 | Torrance et al. | 606/170 |
| 7,713,231 B2 * | 5/2010 | Wulfman et al. | 604/93.01 |
| 7,771,445 B2 * | 8/2010 | Heitzmann et al. | 606/159 |
| 2001/0004700 A1 * | 6/2001 | Honeycutt et al. | 606/159 |
| 2002/0007190 A1 * | 1/2002 | Wulfman et al. | 606/167 |
| 2002/0058956 A1 * | 5/2002 | Honeycutt et al. | 606/159 |
| 2004/0006358 A1 | 1/2004 | Wulfman et al. | |
| 2004/0181249 A1 * | 9/2004 | Torrance et al. | 606/170 |
| 2004/0220519 A1 * | 11/2004 | Wulfman et al. | 604/93.01 |
| 2004/0235611 A1 * | 11/2004 | Nistal | 475/331 |
| 2004/0236312 A1 * | 11/2004 | Nistal et al. | 604/533 |
| 2004/0243162 A1 * | 12/2004 | Wulfman et al. | 606/167 |
| 2010/0174302 A1 * | 7/2010 | Heitzmann et al. | 606/159 |

* cited by examiner

INTERVENTIONAL CATHETER ASSEMBLIES, CONTROL SYSTEMS AND OPERATING METHODS

CROSS-REFERENCE TO RELATED APPLICATIONS

This application is a divisional of U.S. patent application Ser. No. 12/769,587 filed Apr. 28, 2010, which is a divisional of U.S. patent application Ser. No. 10/798,621 filed Mar. 10, 2004 and issued May 11, 2010 as U.S. Pat. No. 7,713,231, which claims priority to U.S. Provisional Patent Application No. 60/453,846 filed Mar. 10, 2003. The disclosures of these applications are incorporated herein by reference in their entireties.

FIELD OF THE INVENTION

The present invention relates to systems for removing material, such as obstructions and partial obstructions, from an internal lumen or cavity of a mammalian subject, such as a blood vessel, a portion of the gastrointestinal tract, dural spaces, and the like. More particularly, the present invention relates to interventional catheter assemblies having mechanisms for advancing and/or rotating an operating head at a target material removal site, aspirating fluid and debris from a target removal site, infusing liquid and debris from a target removal site, and control systems for use with such interventional catheter assemblies.

BACKGROUND

Removal of disease such as atherosclerotic plaque, thrombus, and other types of obstructions and partial obstructions from internal body lumens or cavities is a well-established interventional technique. Numerous interventional catheters have been conceived and developed. Most of these systems require placement of a guiding catheter and guide wire prior to introduction and placement of the interventional catheter at the target operating site. Advanceable and/or rotating operating heads have been used to cut and/or ablate obstructions. Many of these prior art systems incorporate aspiration systems to remove the ablated material from the site.

Despite the many and varied approaches to material removal systems, many challenges remain in providing systems for removing material from a lumen, such as a blood vessel, safely and reliably and without causing complications. The safety and reliability of the system is manifestly critical. Recovery of debris generated during a material removal operation, or maceration of the debris to a particle size that will not produce blood vessel damage or embolic events is essential. The flexibility and size of an interventional catheter is also an important feature. The system must be small enough and flexible enough to navigate through sometimes tortuous internal structures and passageways, such as blood vessels, for placement at the target interventional site. The interventional catheter must also have sufficient stiffness and integrity to operate reliably at high rotational rates while allowing for aspiration and/or infusion of fluids to the site.

In interventional catheters that employ a "cutting head," any cutter structures must be benign during navigation of the operating head to and from the target site, yet effectively remove material during the operation. In addition, cutter structures must effectively remove disease or undesired material without damaging delicate neighboring tissue, such as blood vessel walls or other healthy tissue, which often surrounds the undesired material. Thus, it is important for cutter structures of the interventional catheter to accurately and reliably differentiate between the disease or undesired material and healthy tissue.

The extent and consistency of the disease or undesired material forming an obstruction are frequently not well characterized prior to an intervention. Thus, although interventional catheters and cutter assemblies having different sizes and material removal properties may be provided, and may even be interchangeable on a material removal system, it is difficult to ascertain which combination of features will be most effective in any particular intervention prior to insertion of the device. Various quick-connect systems have been developed to permit removal and installation of multiple operating catheters during a single surgical intervention. This is not ideal, since the interchange, requiring withdrawal and insertion of multiple interventional catheters, is time consuming and increases the risk of the operation. Having access to multiple cutter assemblies having different sizes and different material removal properties on a single interventional operating catheter is highly desirable.

Many prior art interventional catheters are intended to be entirely disposable. That is, the catheter tube, operating head, drive and control mechanisms are provided as sterile, single use, disposable systems. Because such systems have rigorous operating and control requirements, providing an interventional catheter and control assembly as a single-use, disposable system is expensive. It would be desirable to reuse some of the operating and/or control mechanisms without sacrificing sterility and operational convenience.

Several prior art interventional catheters provide for aspiration of liquids and/or debris from the material removal site. In general, such aspiration is provided by a vacuum pump or, in many cases, by an evacuated recovery vessel, such as an evacuated bottle. These systems tend to provide inconsistent and variable vacuum during operation, which reduces the efficiency and effectiveness of the material removal operation and, under certain circumstances, may compromise the health of the patient.

The operation of an advanceable, rotatable operating head is generally under the control of a physician or other professional using some type of a sliding advancement mechanism operated within the sterile field. Advancement of a rotatable operating head to remove undesired material must generally be carefully coordinated with rotational control of the operating head. Rotational speed displays may be provided in the form of an rpm gauge on a control module. Advancement of the operating head is often visualized on a separate display.

Although interventional catheters are used frequently, limitations in the flexibility, reliability and versatility of existing systems limit the types of disease conditions that can be effectively treated. The interventional catheter assemblies and control systems of the present invention have been designed to overcome these limitations.

SUMMARY OF THE INVENTION

Interventional catheters of the present invention incorporate an operating head mounted at or near their distal ends to cut or abrade or otherwise break down undesired material at a target intervention site. The operating head may have cutting surfaces or blades, such as a cutter assembly having one or more differential cutting surfaces. Although the "cutting" surfaces or blades of interventional catheters of the present invention may be sharp and may actually "cut" material at the target site, the term "cut" or "cutting," as used herein, refers to cutting, scraping, ablating, macerating and otherwise breaking down undesired material into removable particles or smaller, removable units of material. "Cutters," "cutter assemblies," "cutting surfaces" and "blades" likewise refer to structures for cutting, scraping, ablating, macerating and otherwise breaking down material into smaller pieces. The operating head is operably connected to a rotatable and axially translatable drive shaft, drive system, aspiration source, and various control systems.

As used herein in the description of various components, "proximal" refers to a direction toward the system controls and the operator along the path of a drive system, and "distal" refers to the direction away from the system controls and the operator and toward or beyond a terminal end of the cutter assembly. In one embodiment of an interventional catheter assembly of the present invention, a cutter assembly comprises at least one differential cutting surface positioned at or near the distal end of the interventional catheter system.

Interventional catheters of the present invention preferably include an aspiration system for removal of debris from the intervention site, generally via aspiration through one or more material removal ports in the cutter assembly or another component in proximity to the cutter assembly. Debris generated during a material removal operation is removed by aspiration through the material removal ports and withdrawn through a sealed lumen of the interventional catheter. The sealed lumen is connectable to a vacuum source and aspirate collection system. The material removal ports may be disposed between blade surfaces of the cutter assembly.

Liquid infusion may be provided in proximity to the cutter assembly in addition to or alternatively to aspiration. Infusion of liquids may be used to provide additional liquid volume for removal of debris, or to deliver lubricating fluids, treatment agents, contrast agents, and the like. Infusion of fluids in proximity to the area of a material removal operation may be desirable because it tends to reduce the viscosity of the materials being removed, thus facilitating removal through relatively small diameter lumens. Infusion of liquids also desirably tends to reduce the volume of blood removed during the operation. According to one embodiment, a sealed lumen formed between the cutter assembly drive shaft and a catheter may alternatively and selectively be used as aspirate removal system and an infusion system. The sealed lumen may thus be selectively connectable to a vacuum source and aspirate collection system for aspiration, and an infusion source for infusion of liquids. Ports in or in proximity to the cutter assembly may be thus employed, selectively, as aspiration and infusion ports.

Interventional catheter assemblies of the present invention incorporate various control systems that, in combination with other features, provide enhanced system efficiency, reliability, versatility and useability. In one embodiment, the interventional catheter assembly comprises a control module that is reusable and operates outside the sterile field in combination with a control pod in which the interventional catheter is mounted. Using this system, expensive and heavy system components and controls can be centralized in the control module, which is isolated during operation, and reused.

BRIEF DESCRIPTION OF THE DRAWINGS

Various features of the interventional catheter assembly of the present invention are illustrated by way of example in the figures described below. The figures and detailed description of various aspects of the invention are not intended to limit the generality of many aspects of the present invention.

FIGS. 9A and 9B are fluoroscopic x-ray images of a coronary artery having a removal site, wherein FIG. 9A depicts the nearly totally and diffusely occluded artery before the operation of the removal system and FIG. 9B depicts a cleared artery after use of the interventional catheter assembly of the present invention.

DETAILED DESCRIPTION

Figure 1:
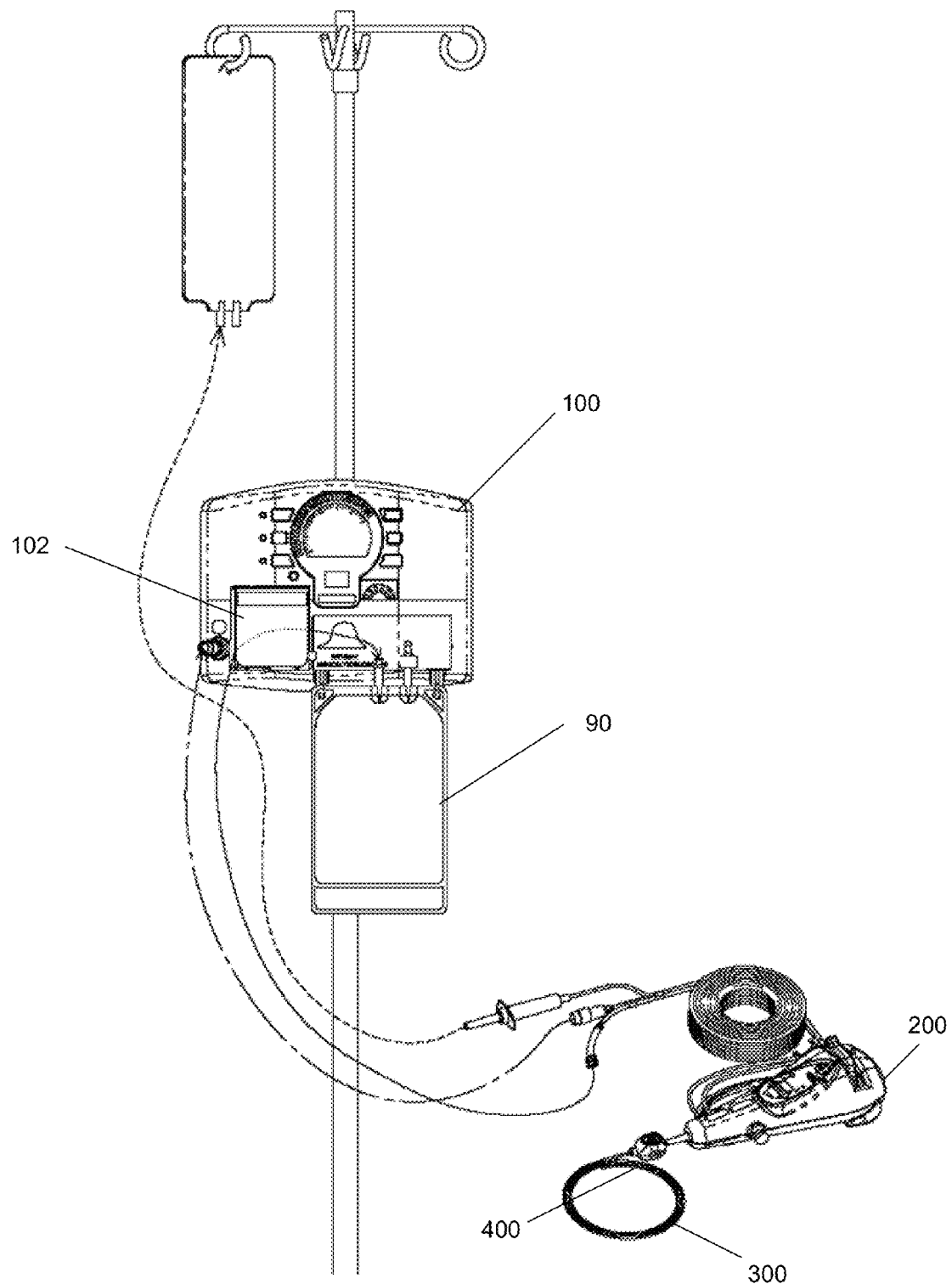
FIG. 1 is a schematic diagram of an interventional catheter assembly comprising an operating head mounted at or near a distal end of a catheter system, a control pod and a console unit, according to one embodiment of the present invention.

Interventional catheter assemblies and control systems of the present invention are suitable for use within any body lumen or cavity that has a sufficiently open space to accept the operating head and is suspected of containing undesirable material. Body lumens and cavities in which such interventional catheters may be used include blood vessels and vascular cavities, gastrointestinal cavities, lumens or cavities in male and female reproductive organs, other fluid cavities such as gas exchange cavities, nasal and sinus cavities, and the like. The lumen or cavity may be a generally tubular-shaped structure, such as blood vessel, or another lumen structure, such as a ureter, a fallopian tube, a nasal passageway, and other tubular passageways. For example, systems of the present invention may be used for removing undesired material from native blood vessels such as native coronary, renal, cranial, peripheral and other blood vessels, artificial or grafted vessels such as saphenous vein grafts, and the like. The body cavity may also be within or in proximity to an organ, such as a kidney, gall bladder, lung, or the like, or the body cavity may form part of another system, such as a lymph node, spinal canal, etc. Interventional catheters are generally used with mammalian subjects, particularly human patients. The undesired material that is removed using interventional catheter assemblies and control systems of the present invention may be disease material such as atherosclerotic plaque, calcified plaque, thrombus, gallstones, a valve or portion thereof, and the like.

The present interventional catheter assembly includes an operating head and catheter system that are inserted and navigated within a patient's body while an operator controls the system externally of the operating head and catheter system. Fluidic communication between the operating head and externally positioned components of the system is generally provided by one or more sealed passageways of a catheter system. Other types of communication systems or pathways may also be provided for delivery of power, control features, and the like. The operating head may be driven, or controlled, using electrical systems, radio frequency and other remote forms of control systems, mechanical systems, magnetic systems, and other systems or mediums that are in use now or may be developed in the future for remote operation of an operating head. The system components described below are described as exemplary components and are not intended to limit the scope of the invention.

Exemplary operating heads, cutter assemblies and blades, bearings, components, and subassemblies suitable for use in connection with the interventional catheters and control systems of the present invention are disclosed and described in publications incorporated herein by reference, including U.S. Pat. No. 6,565,588B1 and PCT Patent Publication WO 01/76680, and numerous other patent publications. The components, subassemblies and control systems of the present invention may be used with interventional catheters having any type of operating head. Operating heads having advanceable, rotatable cutter surfaces at near their distal ends are especially suitable for use with the interventional catheter and control systems of the present invention. The operating head is provided at or near a distal end of the interventional catheter and is guided to and from a desired material removal site through internal passages, such as blood vessels, as is well known in the art. At the target removal site, the operator head is actuated remotely by the operator to cut, grind or ablate, or otherwise separate and break down or remove undesired occlusive material. In many embodiments, the occlusive material is removed the site by means of an aspiration system or another debris removal system.

The interventional catheter system is generally used in conjunction with a flexible guidewire that is navigated through internal pathways, such as blood vessels, to a target material removal site. For partial obstructions, the guidewire is generally placed across the lesion and the operating head of the interventional catheter is advanced, on the guidewire, to the target site and then into and through the lesion. When a lumen is totally obstructed and a guidewire can't penetrate the obstruction without causing harm to nearby tissue or risking embolization, the operating head may be advanced beyond the distal tip of the guidewire and into and through the obstruction, or the operating head and guidewire may be advanced in tandem. Although a guidewire is a conventionally used steering system for interventional catheters, other methods for guiding and steering the operating head may be used, such as radio frequency systems, stereotactic systems, magnetic systems, remote control systems, and the like. Interventional catheters may be adapted for use with any of these steering systems.

FIG. 1 depicts an exemplary embodiment of an interventional catheter assembly and control system of the present invention. In general, an operating head 400 is provided at or near the distal end of a catheter system 300 for insertion into a body and navigation to a target material removal site. The catheter system 300 is operably coupled to the operating head 400 at or near a distal end and to a control pod 200 at or near a proximal end. A drive shaft may also be operably coupled to the operating head at or near a distal end and operably coupled to a drive system housed within control pod 200. The drive shaft may be provided in association with one or more sealed conduits and/or layers providing withdrawal of liquids and debris from the target site or delivery of liquids to the target site, as is known in the art. Control pod 200 houses operational and/or control components, such as a drive system, a system for translating torque from a motor drive to the drive shaft when a motor drive is used, a system for actuating and/or advancing the operating head, a guide wire clamp, one or more connectors for conduits, and/or operator controls. A slidable drive motor actuator 220 may optionally be provided coupled to the catheter system and the operating head drive system to control operation and/or advancement of the operating head.

Various communications pathways, such as liquid and/or electrical conduits, extend between the control pod 200 and a console unit 100 that houses various operating and control systems. A liquid conduit for collecting debris and liquid during operation of the operating head is in communication with a liquid receptacle 90, for example. Liquid infusate source 94 may also be provided to provide fluid to the system, when desired. Console unit 100 incorporates various controls and displays and houses a vacuum or aspiration motor 102. Console unit 100 may also provide a power source for operating the operating head and system components, or it may be in communication with an external power source.

Figure 2:
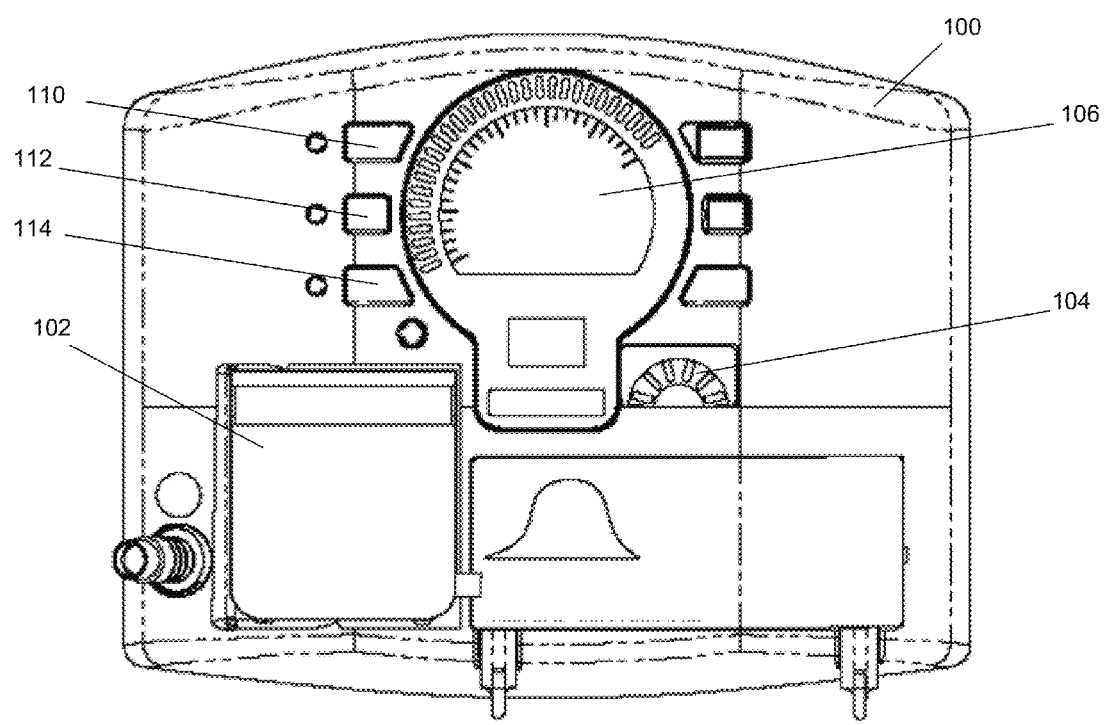
FIG. 2 illustrates the control and display features of a console unit of the present invention.

An exemplary console unit 100 is shown in more detail in FIG. 2. Various software components, e.g. applications programs, may be provided within or in communication with the console unit, that cause a processor or other components to execute the numerous methods employed for controlling operation of the interventional catheter. The software may be provided in a machine-readable medium storing executable code and/or other data to provide one or a combination of mechanisms to process user-specific data, according to one embodiment of the invention. Alternatively, various systems and components may be controlled using hardware or firmware implementations. Data storage and processing systems may also be provided in console unit 100.

One function of the console unit is to provide feedback of system or environmental conditions or operating parameters. The console unit may output operational information concerning operating conditions and feedback from the material removal site to the operator. According to one embodiment, the console unit provides continuously updated output to an operator of operating parameters such as cutter head rotation rate, which may include the actual run speed as well as the desired speed; advance rate; aspiration rate and/or volume; infusion rate and/or volume; length of the body or matter to be removed that is traversed; and the like. In one embodiment, a fluid flow sensor, such as a Doppler device, may be also included in the system and fluid flow at the target site may be monitored and displayed.

Certain automated and selectable control features may be implemented in console unit 100. Preset routines or programs involving various operating parameters may be preselected, stored and selectable by an operator, for example. Thus, according to one embodiment, a material removal system of the present invention implements control features based on an operator's input of specified parameters. Specified parameters may include, for example: lesion length, lesion type and character, such as calcified, fibrotic, lipid/fatty, and the like; and/or historical factors, such as restenosis; rate of blood flow; volume of blood flow; percentage of restriction; lumen type and/or location; lumen diameter; desired rotation rate and/or rotation profile for the cutter assembly; desired advance rate and/or advance profile for the cutter assembly; desired aspiration rate and/or profile; desired infusion rate and/or profile; and the like. Based on the specified parameters input by the operator, an automated cutter assembly control unit may calculate and implement automated operating conditions, such as: cutter assembly rotation rate and profile; cutter assembly advance rate and profile; aspiration rate and profile; infusion rate and profile; cutter assembly size and type; and the like. Various system operating parameters may also be recorded and stored during interventions to preserve a record of the operational parameters.

Aspiration pump 102 may be provided in association with console unit 100 and, in this embodiment, console unit 100 is preferably provided as a reusable system component. High efficiency aspiration is important in the interventional catheter systems of the present invention. Aspiration pump 102 is preferably capable of providing constant, high levels of aspiration of liquids and/or liquid/debris mixtures, at rates of at least 15 ml/l through small catheter systems when the aspiration site is remote. In exemplary interventional catheter systems of the present invention, for example, the aspiration site may be more than a meter away from the control pod through an aspirate removal passageway having a diameter of less than 0.10 inch and more often between about 0.050 to 0.070 inch, and more typically about 0.065 to 0.066 inch. The distance that aspirate travels between the control pod and the console unit may be from about 0.4 to several meters, through an aspirate conduit that is between about 0.125 to 0.94 inch in diameter. The blood and debris being aspirated are relatively viscous fluids. Achieving a relatively constant and high level of aspiration under these conditions is essential.

In one embodiment, aspiration pump 102 comprises a multi-lobed roller pump. At least three rollers, or lobes, are preferably incorporated in the roller pump. The rotation rates of multiple rollers or of a multi-lobed rotating structure may be variable or selectable to control the aspiration rate and volume. Roller pumps permit fluid to flow in conduit through the rollers of the pump at atmospheric pressure, and thus reduce or prevent the formation of bubbles and foam in the liquid being evacuated. Because the aspirate is at atmospheric pressure when it exits the roller pump, a simplified, atmospheric pressure collection vessel may be used rather than an evacuated collection vessel. A simple bag or another collection vessel, such as those used for collection of blood, may be used. Collection bag 90 may be provided having a sealed conduit that is mounted in the roller pump and connected to an aspirate withdrawal site at the control pod during operation. In this embodiment, the aspirate collection bag and sealed conduit may be provided as part of the sterile disposable interventional catheter system and simply mounted on the aspiration pump prior to operation.

In another embodiment, the aspiration pump may comprise multiple vacuum pumps aligned in series to provide a consistent and high level of aspiration. In this manner, each pump incrementally increases pressure when it is operated in conjunction with other pumps in the series. Alternatively, the aspiration system may comprise multiple series of pumps connected in parallel. This system may also provide a consistent, high level of aspiration.

Console unit 100 may house a power source or provide communication to an external power source. In the embodiment illustrated in FIG. 2, an electrical device port is provided for providing electrical power to the control pod. An electrical conduit may be provided mounted to electrical components in the control pod and connected to the console unit prior to operation. Console unit 100 also has a power on/off switch that controls power to the device port.

In addition, console unit 100 may include control status indicators to show the status of various system components and/or controls. For example, one or more operating head status indicators may show the real-time status of the operating head. In the console unit of FIG. 2, for example, an operating head status indicator 104 shows whether the operating head is at a minimum or maximum diameter during any operation. Console unit 100 also has a speed gauge 106 to display that actual rotational speed of a rotating operating head during operation. An analog gauge may be provided, as well as a digital gauge that shows the numerical value of rpm. The rotational speed of the operating head changes in real time to reflect the actual operating head speed as it is advanced through an obstruction. Console unit 100 may also have control switches for activating and shutting down the aspirate withdrawal pump and system, and for activating and shutting down an infusate system. These control features are generally provided as simple switches, though selectable levels of aspiration and/or infusate may be provided. Console unit 100 may also be provided with a timing mechanism that determines, and displays, the elapsed time of operation of the operating head and/or the aspiration system. The volume of aspirate withdrawn may also be displayed.

Console unit 100 may also be provided with one or more selectable torque features. The selectable torque features permit an operator to determine the torque, or power, delivered to the operating head separately from the rotational speed and thus provides an additional level of operator control and safety. In an operating head having cutting blades, for example, operation of the cutter assembly at a high torque setting may provide overly aggressive removal of undesired material and damage healthy tissue. Some lesions that are composed of very hard material may require operation at a high torque setting, and some cutter assemblies do not damage healthy tissue even when operated at a high torque setting. It is therefore highly desirable and increases the versatility of the interventional catheter system to provide selectable torque levels for operating the operating head. The selectable torque control features may be provided at the console unit, as shown, or they may be provided at the control pod.

Selectable torque control features may be provided by limiting the current provided to the operating head drive system. In one embodiment, for example, a maximum torque or power control setting 110 allows a preselected current level, such as 1.1-1.5 amps, to be provided to the operating head drive system. A medium torque or power control setting 112 may provide a preselected current level of from 0.7-1.3 amps to the drive motor system. A minimum torque or power setting 114 may provide a preselected current level of less than 1 amp to the drive system. In a control system having selectable torque features, an additional override control feature may be provided. In this system, control circuitry is provided so that when the current level required to maintain a desired rotational speed at the operating head exceeds a predetermined value, power to the operating head is inactivated and the operating head stalls. If additional power is required to remove obstructive material, the torque setting may be changed and the operating head activated and advanced into the lesion at the higher torque setting. Different preselected torque override values may be applied to each of the selectable torque settings and, if the system is programmable, may be changed by an operator prior to use. A torque or power gauge may be provided as an analog or digital gauge on the console unit or control pod to show the actual torque delivered to the operating head as current drawn by the motor drive system The selectable torque control feature greatly enhances the versatility and safety of the interventional catheter assembly.

In one embodiment, console unit 100, including aspiration pump 102, is provided as a separate, re-usable unit. The console unit may therefore be purchased as standard equipment in operating rooms, for example, and the interventional catheter assembly comprising the control pod, the catheter system and operating head may be provided as sterile, single use systems. In the systems illustrated, the console unit isn't contaminated by contact with blood or aspirate during operation, the power and control systems are durable and long-lasting, and so the console may be reused for many interventions. The console unit may be provided in a housing designed to sit on a platform during operation, or the housing may be designed for mounting on a structure, such as an iv pole or another structure during operation. An aspirate collection vessel may be mounted to the console during operation, or to an associated structure. Similarly, an infusate source may be mounted to the console or to an associated structure. In another embodiment, a tracking pod and motor activation button may also be provided as a reusable unit.

Figure 3A:
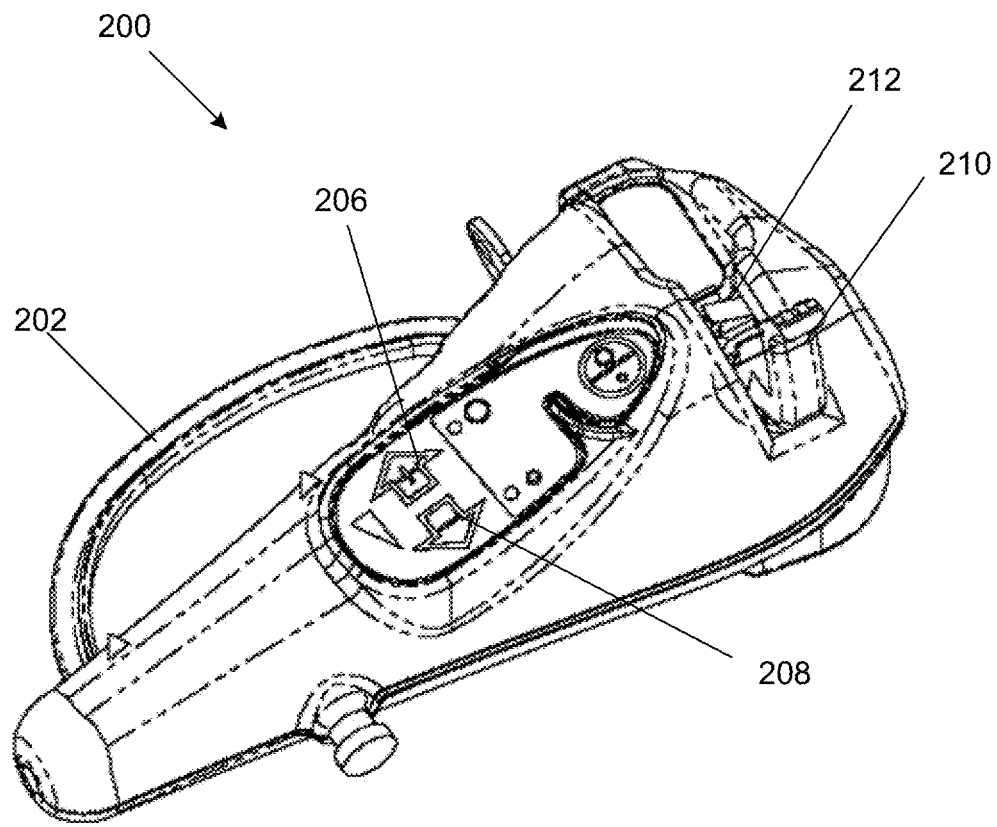
FIG. 3A illustrates a certain control and operational features of a control pod of the present invention.

The control pod 200 is illustrated in more detail in FIG. 3A. Control pod 200 is optionally electrically connectable to a power source, such as an electrical power source at or in communication with console unit 100. Control pod 200 is also in fluid communication with aspirate collection vessel via a fluid conduit, and the drive shaft, aspiration conduit and catheter system all traverse and/or exit from control pod 200, for example, at a distal end of the pod. Control pod 200 is constructed from a durable, sterilizable material, such as hard plastic, and may be provided in any convenient ergonomic design and constructed for placement in proximity to and/or in contact with the external body. In one embodiment, the control pod may include an integrated handle or support 202 for convenience in holding and supporting the control pod during operation. The control pod is preferably compact and may have a generally triangular configuration, as illustrated in FIG. 3A.

The control pod, as shown, is intended to be used within the sterile field during operation and is provided as part of the interventional catheter assembly. It will be noted, however, that some of the control and operational features of the control pod may be provided in the console unit and, likewise, some of the control and operational features of the console unit may be provided in the control pod.

In the embodiment of FIG. 3A, control pod 200 houses a drive motor providing torque and rotation to the drive shaft and operating head. The drive motor may be of many types, such as electrical, pneumatic, or the like. Electrical, direct current variable speed drive motors are preferred for use in interventional catheter assemblies of the present invention because they reliably provide high power and high torque, yet numerous control systems can be implemented. Preferred drive motors deliver a constant voltage source for any given rotational output. If, under load conditions, the voltage employed to produce a given rotational output isn't sufficient, the motor system adjusts current delivered to the system to achieve the desired rotational output. The voltage delivered to the drive system is thus regulated according to the desired rotational output. In preferred embodiments employing selectable torque features, the current delivered to the drive system is regulated, and limited, by the torque selection. Preferred motor systems employ cascaded variable regulator voltage sources. The motor system may provide bi-directional output.

The rotational output of the drive motor is preferably adjustable by the operator to control rotation of the operating head. Rotational speed of the drive motor, drive shaft and operating head may be adjusted at control pod 200 at speed up and down controls 206 and 208. In many interventional catheter applications, the drive shaft and operating head are rotated at high speeds. For example, rotational speeds of from several hundred to 100,000 or 200,000 rpm may be required. When the drive motor provides bi-directional output, a direction of rotation selection may be provided at the control pod. Similarly, if the operating head operates in more than one configuration, an operating head selection may be provided at the control pod. In a preferred interventional catheter assembly of the present invention, the operating head comprises a cutter assembly that is adjustable between a smaller diameter and a larger diameter condition. A selection switch for tip size may be provided at the control pod. Tip size may be controlled by changing the direction of motor drive rotational output.

Delivery of rotation to the operating head drive shaft from the motor output shaft is important in interventional catheter assemblies that have advanceable, rotatable operating heads, and must be accomplished so that the drive shaft is simultaneously advanceable and rotatable. Mounting of the operating head drive shaft off-axis with respect to the output shaft of the motor drive using suitable gearing systems permits translation and advancement of the drive shaft independently from the drive system, which allows the drive system to remain stationary during operation of the interventional catheter.

Figure 4:
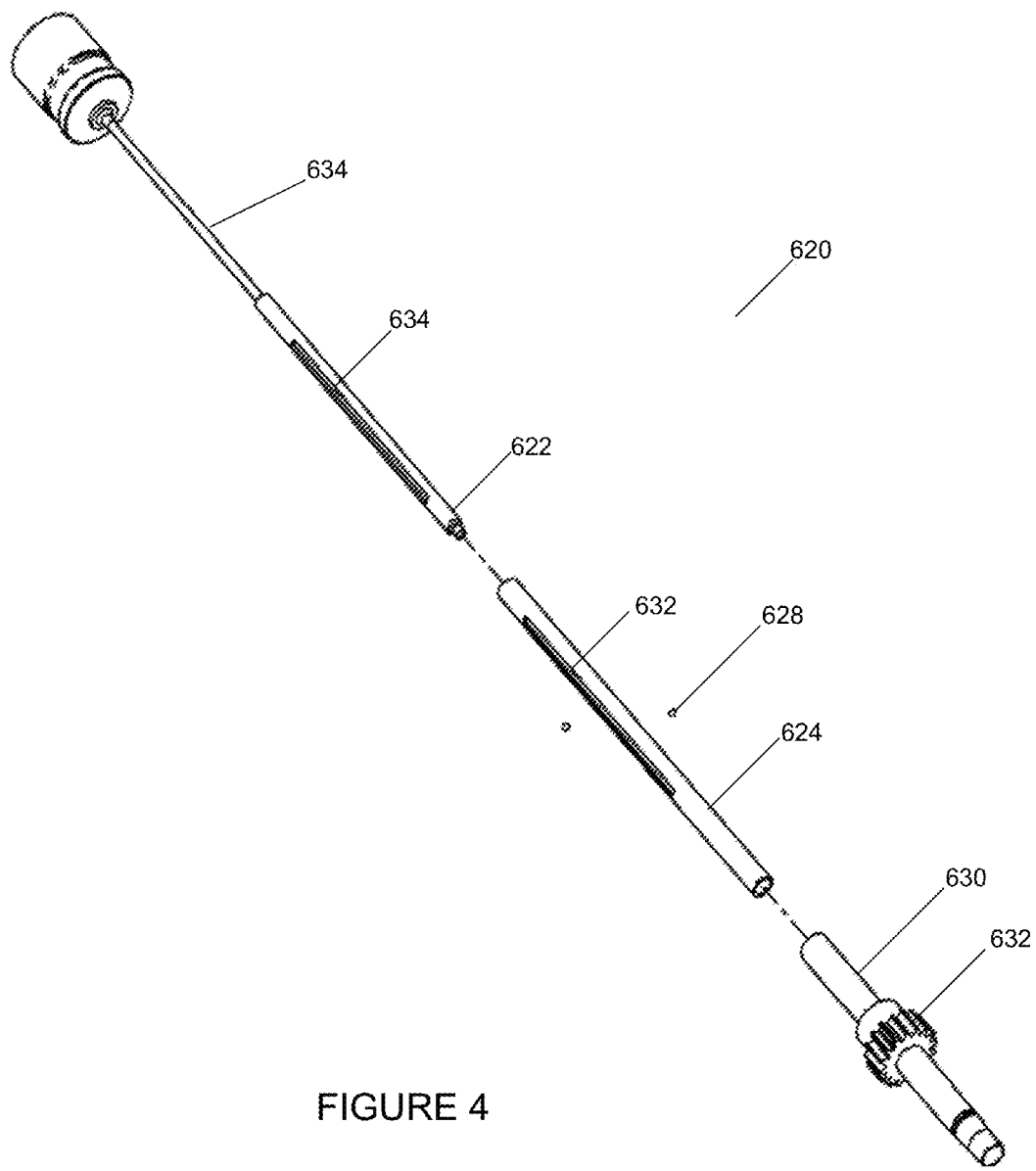
FIG. 4 illustrates an enlarged, exploded perspective view of a sliding, rotatable torque transmission system of the present invention.

In one embodiment of a torque transfer system of the present invention shown in the exploded view of FIG. 4, a torque transfer sliding tube system 620 may be provided for transferring torque to the drive shaft. The torque transfer system both provides torque to the drive shaft and permits smooth axial translation of the drive shaft, even at high rotational speeds. The sliding tube torque transfer system also allows the catheter system to advance over a guidewire without the drive shaft disengaging from the motor drive assembly and while a guide wire locking device maintains the guide wire position. Experimental work has also demonstrated that the sliding tube torque transfer system of the present invention may provide an operator greater and more realistic tactile feel for safe and effective removal of undesired material during operation of the operating head as the lesion when a sliding tube torque transfer system is used in the interventional catheter assembly.

Sliding tube torque transfer system 620 comprises a rigid inner tube or cylinder 622 and a rigid outer tube or cylinder 624 that is axially slidable over at least a portion of the inner tube. Each of the tubes is provided with at least two matching slots 632, 634 generally arranged in a radially symmetrical arrangement, with a ball bearing 628 being slidably retained between each set of slots. The inner and outer tubes are sized so that when a ball bearing is placed between each of the matching slots, the tubes are both axially slidable and rotatable with respect to one another. Slots 626 preferably extend for most of the length of inner tube 622, so that the inner and outer tubes are slidable with respect to one another along most of the length of inner tube 622. The slot of the outer tube usually extends through the body of the tube and does not include a bottom surface. A proximal end of the outer tube may be operably coupled to a pinion shaft 630 of the drive system. The pinion shaft 630 transfers torque to the outer tube and retains the ball bearings. The pinion shaft 630 includes at least one gear 632 to operatively couple to a drive system gear. Rotational torque is transferred from the pinion shaft, to the outer tube and, through the ball bearings being positioned in the aligned channels, to the inner tube and then to a drive shaft. The catheter system may be mounted to the inner tube, such as through a main shaft 634, which allows smooth translation of the catheter even during high rotational operations.

Control pod 200 also includes a system for preventing gases, such as air, from being drawn into structural elements that move relative to one another and into the catheter system. Preventing air leakage into the system and preventing any resulting loss of pressure in a high vacuum zone is especially important in catheter systems employing high aspiration rates and requiring relatively high vacuum levels to effectively aspirate fluids and debris from the material removal site. In one embodiment, a liquid seal is established in proximity to the rotating drive shaft. This system is illustrated in FIGS. 5 and 6A-6B.

Figure 5:
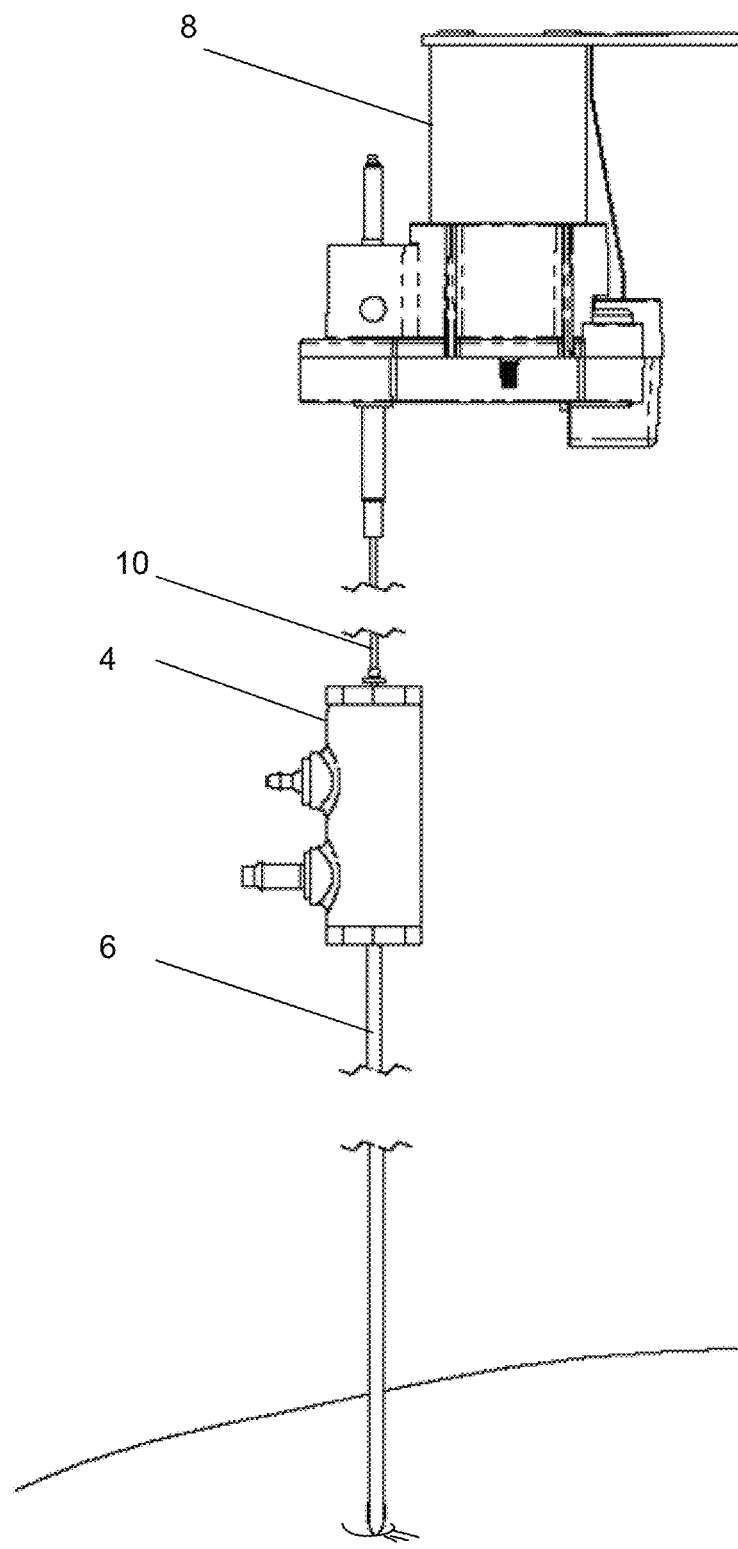
FIG. 5 illustrates, schematically, a fluid seal system for preventing air ingress to the catheter system.

FIG. 5 shows a schematic diagram of the drive system in communication with a liquid seal system of the present invention. Control pod 200 generally houses a drive system 8 that rotates a proximal end of drive shaft 10. The drive shaft 10 then passes through sealing assembly 4 including a high vacuum section and is operably coupled to drive shaft 10. A catheter system 6 surrounds the drive shaft and extends distally to the operating head, enclosing the drive shaft and providing aspirate and/or infusion lumens. The sealing assembly utilizes a drive shaft liner and takes advantage of pressure differentials within the control pod to produce a liquid seal that prevents ingress of air into the catheter system.

Figure 6A:
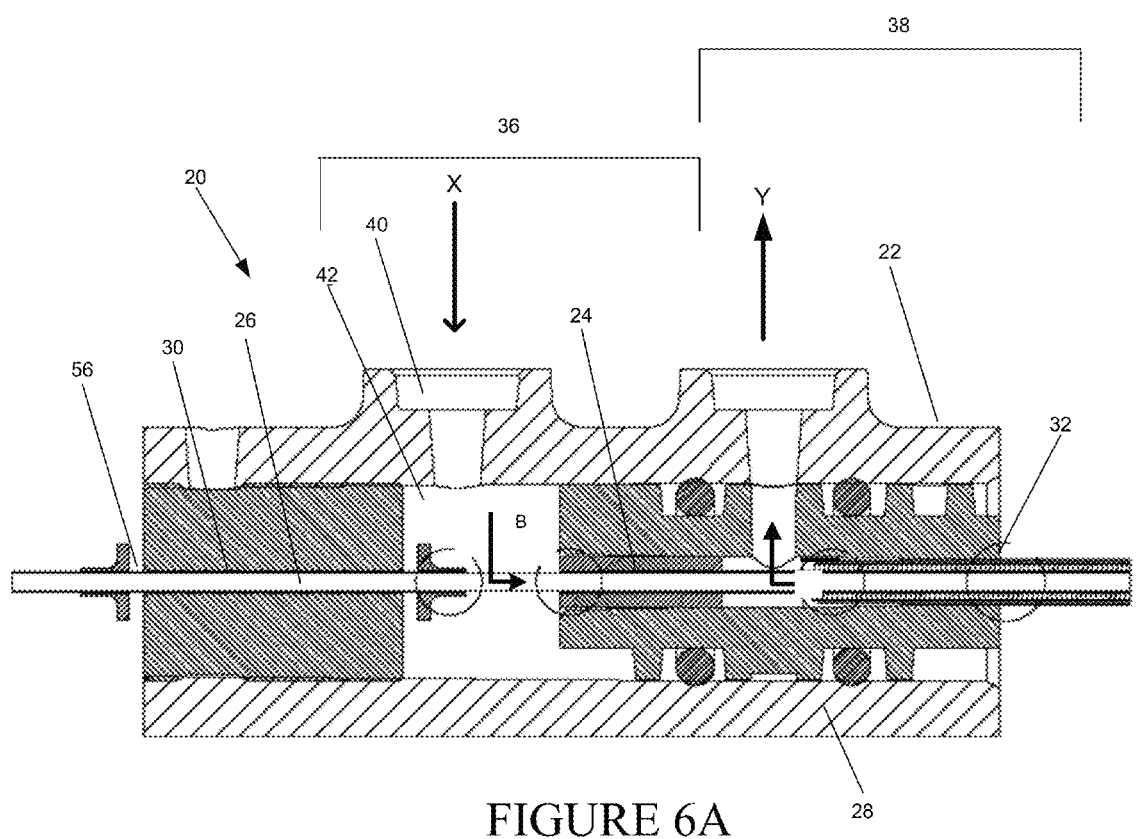
FIGS. 6A and 6B show enlarged, cross-sectional views of various components of a fluid seal system of FIG. 5.

FIG. 6A shows one embodiment of sealing assembly 20 having a sealing member 22 and a liner 24 wrapped around a drive shaft 26. The sealing member includes a housing 28 enclosing one or more sealing sites. The housing is a rigid member that encloses at least a portion of the drive shaft in a manner that permits free rotation and axial translation of the drive shaft. The housing includes a longitudinal bore 30 through which the drive shaft is positioned. The bore includes one or more axially aligned sites that form the one or more sealing/junction sites. At least one layer of the catheter system enclosing the drive shaft passes into the sealing assembly at an aperture 32. The proximal end of the catheter system terminates in the sealing assembly in an aspiration zone 38. The drive shaft continues through the sealing assembly and passes through an exit aperture, such as overflow port 56. Liquid is provided to the sealing assembly at a region of substantially atmospheric pressure. This area is susceptible to leaking air to the neighboring low pressure aspiration zone. The liquid seal prevents air from traveling along a significant length of the drive shaft towards the material removal site. An infusion port 40 supplies reservoir 42 for retaining liquid during operation of the interventional catheter.

Figure 6B:
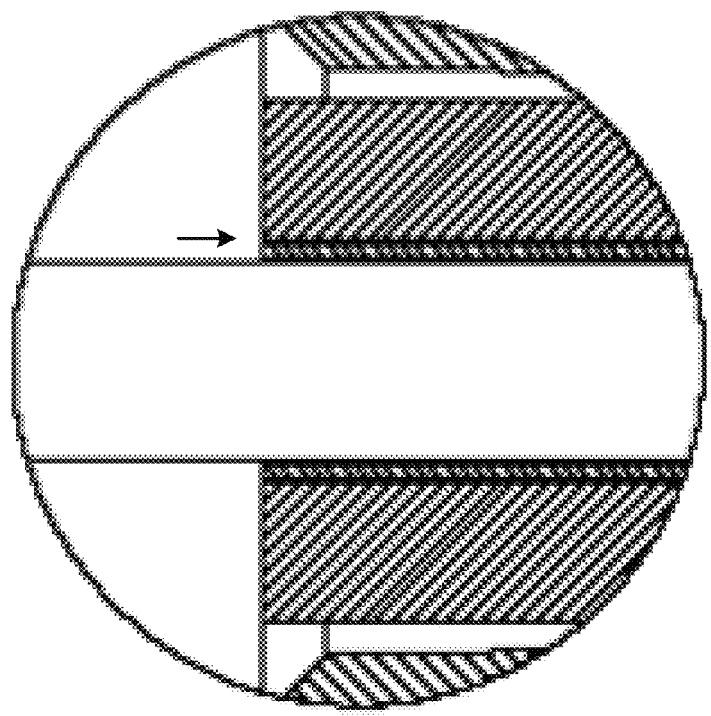

An enlarged view of a portion of a liquid seal site 36 is shown in FIG. 6B. In general, a tubular liner 24 is spaced apart from and surrounds at least a portion of the longitudinal length of the drive shaft. The liner is generally not bonded to the drive shaft so that as the operating head is rotated, the drive shaft is rotate freely, while the liner remains stationary. Surface tension and head loss prevent the liquid from moving very rapidly into or very far along a flood space formed within the inside diameter of the liner, even when high vacuum levels are provided in the aspiration zone. Thus, only a minimal amount of liquid travels the flood space.

The liner may comprise any material that is formable into a thin, tough, flexible, sealed tube. The liner is typically highly compliant so that it follows the contour of the drive shaft without reducing the flexibility of the drive shaft. The liner is supported along its length by the drive shaft, and the liner material therefore need not be stiff or resistant to changes in pressure. The material forming the liner may also be slippery, or lubricious, when wet or when contacting another material. The liner material also possesses high thermal resistance and does not degrade as a consequence of frictional loads created by drive shaft rotation. The liner may comprise conventional, polymer-based tubing comprising, for example, a polyimide material and having a lubricious surface coating, such as a polytetrafluoroethylene (PTFE), such as Teflon®, on at least the inner surface of the liner.

The dimensions of the liner depend, inter alia, on the diameter and design of the catheter system and drive shaft, the characteristics and design of the seal assembly, and the anticipated local vacuum levels required to produce the desired level of aspiration. The clearance between the liner and the drive shaft at the flood space is typically quite small, such as about 0.002 to 0.003 inch. The wall thickness of the liner is typically very small, such as from about 0.001 to 0.0015 inch. The liner extends a distance along the axial length of the drive shaft sufficient to prevent air leakage along the length of the liner. In an exemplary system, the liner may extend for about 1 to 30 inches in length, more typically from about 6 to 25 inches in length. A longer liner is often desirable to minimize, due to head loss, the amount of liquid traveling the flood space and exiting the distal end of the flood space to dilute aspiration. In interventional catheters employing high aspiration rates, the liner may consume some of the available lumen space for aspiration. Where high aspiration rates are desired, relatively shorter liner sections may be provided.

As the interventional catheter is operated, liquid continues to flow into the sealing assembly from the infusion port. Typically, liquid flows from an external liquid source through tubing connected to the infusion port. In one embodiment, liquid drips from a conventional fluid bag that is placed a distance above the sealing assembly and feeds the sealing assembly by gravity flow. Saline and water are common liquids that are suitable for use in the sealing assembly and are conveniently provided in a sterile form. In another embodiment, the liquid may comprise blood and/or plasma that is withdrawn from the patient. For example, blood and/or plasma that is aspirated from the patient through the interventional catheter may be treated by filtration, mixed with agents such as anticlotting or treatment agents and then introduced into the infusion port to provide liquid for the sealing assembly.

Figure 7:
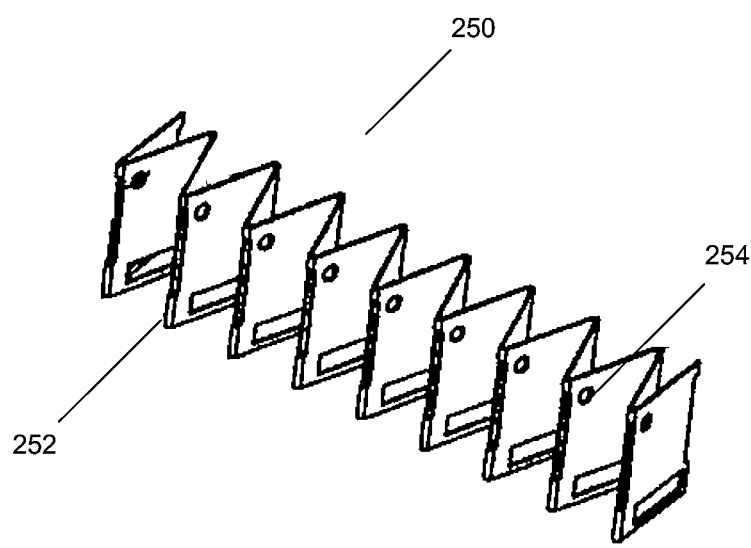
FIG. 7 shows an enlarged perspective view of an extendable guidewire support of the present invention.

Control pod 200 may additionally house an extendable, telescoping guidewire support, which reduces the size requirements of the control pod and provides guidewire support over a variable length. FIG. 7 illustrates one embodiment of a guidewire support 250 comprising a folding assembly having aligned holes for passage of a guidewire. Each panel 252 of guidewire support 250 has substantially the same dimensions, has a guidewire passageway 254 in a location corresponding to guidewire passageways in the other panels, and is foldable along each of its sidewalls with respect to adjacent panels. The guidewire passageways are preferably sized to allow passage of guidewires having a range of diameters.

The guidewire support may be mounted at a proximal end to the motor drive or another structure within the control pod and may be mounted at a distal end to the guidewire brake or another structure within the control pod. The guidewire support is adjustable between a shorter, substantially folded condition and a longer, substantially extended condition as the structures between which the support is mounted move relative to one another. In one embodiment, the guidewire support is adjustable between a shorter, substantially folded condition in which the axial length of the guidewire support is about one inch or less and a longer, extended condition in which the axial length of the guidewire support is about 6 inches or more.

Control pod 200 may also incorporate a guidewire brake or locking device 210, as shown in FIG. 3A, adjustable between a clamping position in which the guidewire is prevented from moving axially or rotatably and a release position in which the guidewire freely passes through the brake, the control pod and the catheter system. The guidewire brake is open, for example, as the guidewire is navigated to and from a target intervention site, while the guidewire brake is clamped after being positioned across a lesion as the operating head is advanced and/or rotated. Guidewire brake 210 may be manually operated or actuated by electrical or electronic systems and preferably accommodates and is capable of clamping and releasing guidewires having a variety of diameters. The guidewire brake may alternatively be provided external to the control pod.

In one embodiment, the guidewire brake position is monitored, for example using an electrical or optical device that senses whether the guidewire brake is in a clamped or a release position. When the guidewire brake is in a release position and the guidewire is freely movable, a control system interrupt prevents the motor drive and aspiration systems from being actuated and, consequently, the operating head is not operable. The control system permits rotation and advancement of the operating head when the guidewire brake is in a clamped condition. This control system interrupt ensures that the guidewire brake is appropriately clamped before the operating head is actuated.

For interventional catheter systems in which it may be desirable to rotate the operating head, for example at low speeds during withdrawal of the operating head from the material removal site of the patient, a selectable interrupt override control 212 may be provided to permit an operator to override the interrupt control and permit translation and/or rotation of the operating head while the guidewire is simultaneously moved. The selectable interrupt override control may be positioned in proximity to the guidewire brake on the control pod or remotely on the console unit, for example.

Figure 3B:
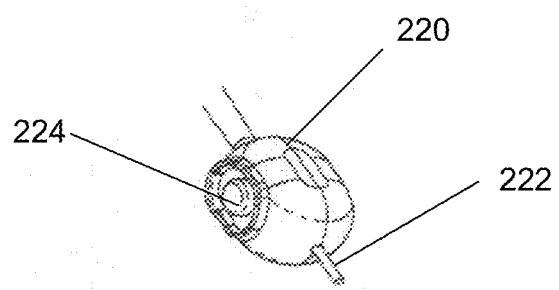
FIG. 3B illustrates a sliding actuator button.

Associate with the control pod, as shown in FIG. 3B, is a slidable drive motor actuator 220. The slidable actuator is slidable over catheter system 222 and is in operable communication with the operating head and drive shaft drive system. The operable communication may be provided by means of an electrical conduit communicating between actuator 220 and the drive system, or communication may be provided by wireless mechanisms. In one embodiment, slidable drive motor actuator 220 incorporates a switch 224 that, when actuated, such as by depressing a button, activates the drive system and/or an aspiration system. When the switch is released, the drive system and/or aspiration system are inactivated.

Slidable actuator 220 also incorporates a clamp mechanism that securely grips the catheter system over which it is slidable when actuated. In a preferred embodiment, the clamp mechanism actuated and released by the same switch 224 that activates the drive and/or aspiration systems. In this system, the sliding actuator may be freely translated along and repositioned on the catheter system when the motor and/or aspiration systems are inactivated. When the switch is actuated, such as by an operator gripping the motor actuator between a thumb and finger and depressing switch 224, the drive system and/or aspiration system is actuated and the catheter system, drive shaft and operating head may be translated, e.g. advanced into or withdrawn from a target operating site and operated to remove undesired material. After one or more operating passes through a lesion are made, the switch may be released, and the actuator may be repositioned on the catheter system for further operating passes through a lesion or other material desired to be removed. This system, providing convenient operator control of both actuation and advancement of the operating head in a single control device, provides improved manipulation of the operating head and precise control features.

A delay may be incorporated between the time the drive system and aspiration system are activated, such that the aspiration system may be actuated immediately upon actuation of the switch, while the drive system may be actuated after a predetermined or selectable delay period. The activation delay period allows the aspiration system to be operating at full aspiration capacity prior to actuation of the drive system and operation of the operating head. A delay period may also be incorporated when the operating head is inactivated, such that the drive system is inactivated immediately upon release of the switch, while the aspiration system may be inactivated after a predetermined or selectable delay period. This inactivation delay period allows the aspiration system to continue operating for a short period after the operating head is inactivated to ensure that all debris is removed from the operating site.

Catheter system 300, exiting the proximal end of control pod 200, is axially translatable with respect to the control pod 200 as the operating head and catheter system are guided to a target material removal site. Flexibility of the catheter system is important, and the catheter system must also have sufficient integrity to prevent collapse of the catheter system during aspiration. All or particular sections of the catheter system may additionally be constructed to provide non-kinking properties. Because the catheter system carries the drive shaft and aspiration and/or infusion lumens, it is essential that the catheter system remain flexible and non-kinking during navigation to the target material removal site, and during operation of the operating head. In one embodiment, a non-kinking, noncollapsing catheter is provided using a multi-layer construction in which a coil constructed from a rigid material, such as a metal, is interposed between and is concentric with an inner flexible tube layer and an outer flexible tube layer.

The coil is preferably only bonded to either the inner or outer flexible layers at one or both ends of the coil and the remaining portion of the coil is free, so that as the multi-layer catheter is flexed, all of the layers are capable of flexing independently of one another. The inner and outer tube layers may comprise any flexible tubular material, such as polyimide, and may have a lubricious coating, such as a PFTE coating on surfaces that contact the coil. In one embodiment, a thermally shrinkable coating that is etched is provided. The coating is applied by shrinking a tube to 25 percent or less of the tube's original diameter prior to heating. The multiple catheter system layers are preferably sized to provide firm contact between adjacent layers and to allow sufficient internal space to provide the required internal lumen(s). The outer flexible layer may be thicker than the inner flexible layer. A non-kinking catheter construction may be provided along the entire length of the catheter system, or along a portion of the length. The portion of the catheter system that exits the control pod when the operating head is positioned near a target site may be particularly prone to kinking, and providing a multi-layer catheter construction of this type at the proximal end of the catheter system is especially suitable.

The catheter system is introduced to a body through an entry system placed to access an internal passageway, such as the femoral artery. Ports are provided in the entry system for passage of the catheter system. The catheter system may be introduced through the port and then translated through the port and guided to the target material removal site. Clamps are generally provided for sealing against the catheter system after placement at the target site. Sealing against fluid leakage from the port is often problematic, however, as the catheter system is guided to the target site. The interventional catheter assembly of the present invention may incorporate a fluid-tight slip seal adapter in its proximal region that slides over the catheter system to seal a connector of the entry system through which the catheter system is guided into the body from fluid leakage.

Figure 8:
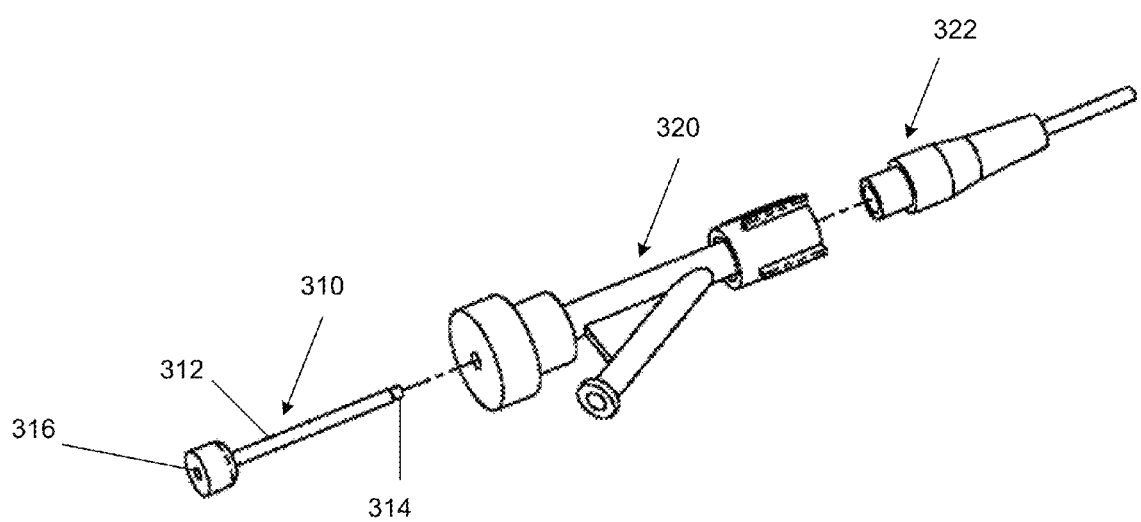
FIG. 8 shows an enlarged perspective view of a sliding, liquid-tight connector used in the interventional catheter assembly of the present invention.

One embodiment of slip seal adapter 310 is shown in FIG. 8, in which at least one catheter may be moveable, such as axially translated, relative to a connector 320. The adapter is inserted within a conventional connector 320 to seal the catheter and a proximal terminal end of a guiding catheter 322. The adapter includes a rigid tube 312 and a thermally shrinkable wrap 314 extending from the tube. A lumen 316 runs through the adapter to permit the catheter to pass through the connector and through the adapter lumen, whereby the shrinkable wrap closely surrounds a portion of the catheter. The shrinkable wrap comprises a lubricious material, e.g. Teflon®, that permits the enclosed catheter to move in a lateral and/or rotational direction and yet maintains the close contact with the catheter. When the shrinkable material is processed, it tightly grips the tube of the adaptor insertion end, while the seal section extending beyond the adaptor insertion end is not supported by the adaptor and shrinks to a diameter that is less than that of the adaptor. The inner diameter of the seal section generally matches the outer diameter of the catheter system and, as a consequence of the lubricious properties of the material, is slidable over the catheter system. Thus, when the insertion end of the slip seal adaptor body is positioned in a port of the entry system connector, the seal section snugly contacts the catheter system and prevents leakage of fluids such as blood, through the port of the entry system. This provides a liquid-tight connection in the insertion system without applying a clamping pressure that deforms or damages the catheter system.

Numerous tests have been conducted using the interventional catheter and control systems of the present invention. For example, the systems have been used to treat acute coronary syndrome and acute myocardial infraction in native coronary arteries. Furthermore, the systems have been used for preparing occluded saphenous vein grafts for accepting a stent. Example 1, described below, shows images of blood vessels before and after a material removal operation, and Example 2 describes laboratory tests demonstrating the aspiration efficiency of an interventional catheter assembly of the present invention.

Example 1

Figure 9A:
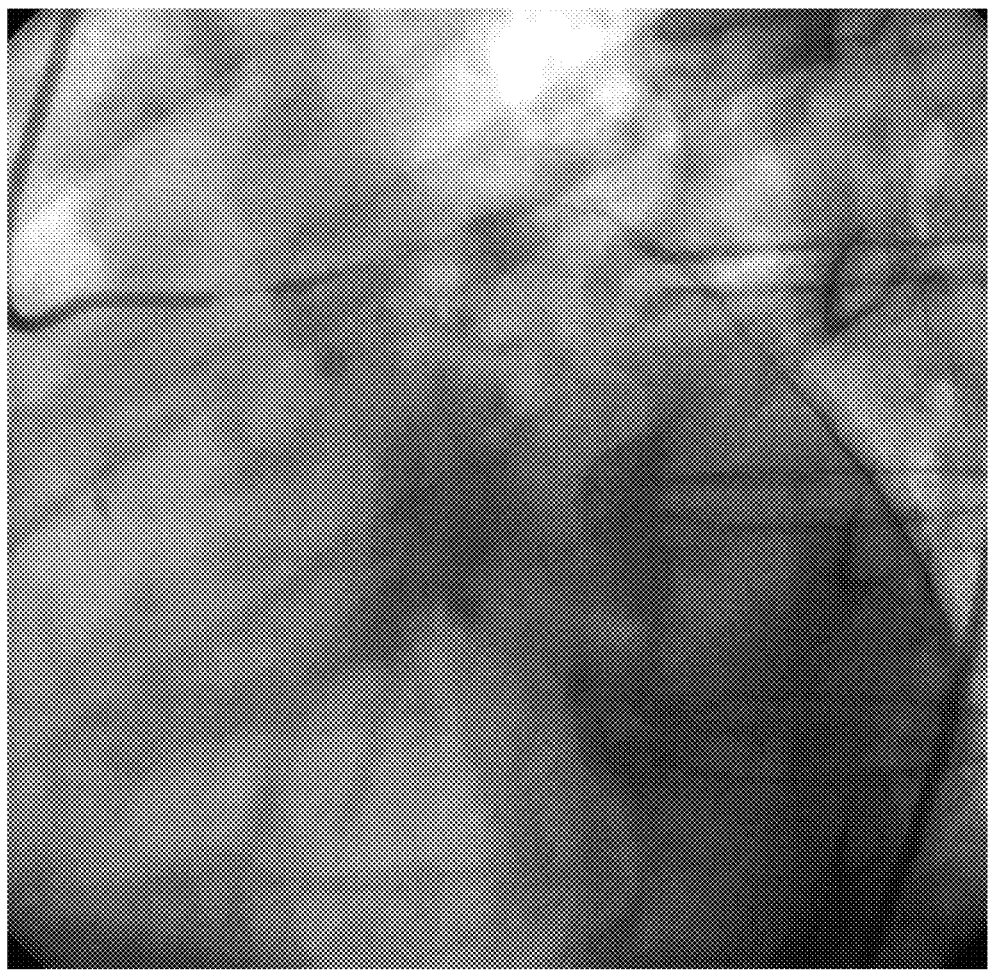
Figure 9B:
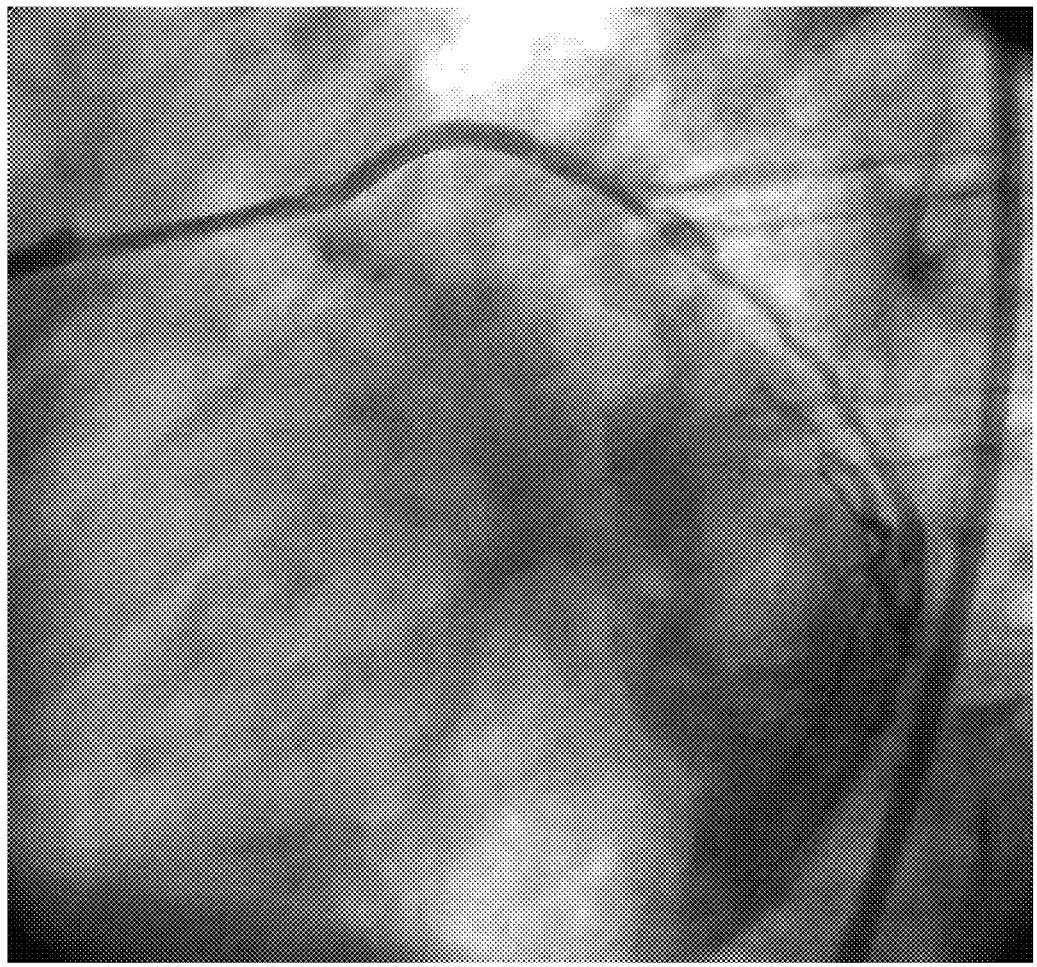

FIGS. 9A and 9B are fluoroscopic x-ray images showing the results of using an interventional catheter assembly of the present invention. FIG. 9A shows a nearly totally and diffusely occluded artery having a coronary bypass graft. The patient was injected with an ionic contrast agent to visualize blood flow and blockages.

The interventional catheter system of the present invention is used to clear the obstruction, often followed by insertion of a stent. A guiding catheter is inserted into the patient and a guide wire was directed to the target site in the artery. The cutter is rotated at 35,000 to 40,000 rpm's while aspirating at the target site. The cutter is advanced with little applied force into the lesion for 3 seconds at a rate of at 1 mm per second. The advancing movement is paused to allow cut particles to be aspirated into the cutter assembly and then the advancing movement is repeated. Contrast agent is applied to the area to visualize the intermediate results of the cutting and to decide on whether to use an expanded diameter of the adjustable cutter on further passes into the target site. A stent is inserted at the target site. FIG. 9B shows the same artery and coronary bypass graft of FIG. 9A, following removal of obstructions using the interventional catheter assembly described herein, followed by stenting.

Example 2

Figure 10:
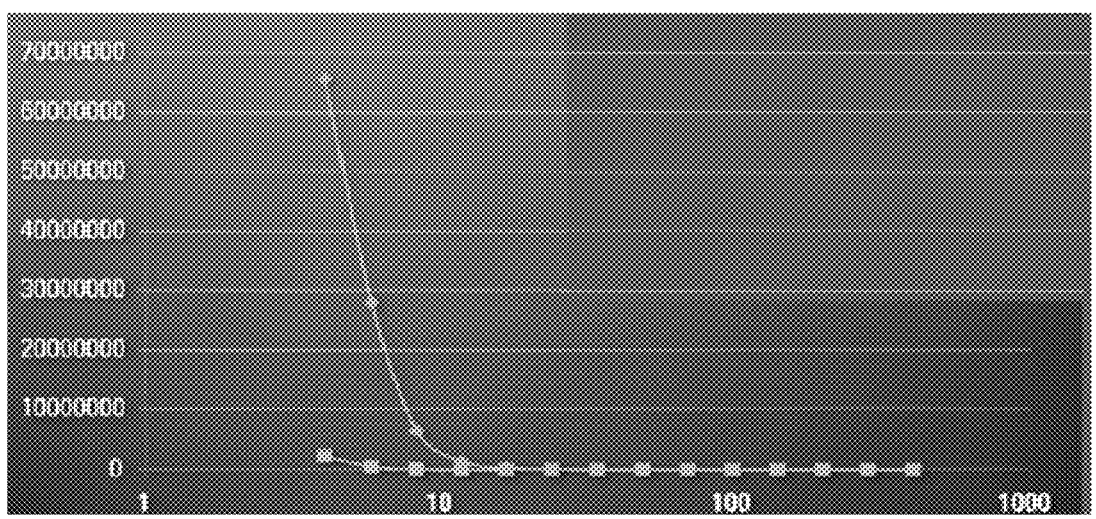
FIG. 10 shows the results of an experimental laboratory simulation in which an artificial lesion was treated using an interventional catheter of the present invention and both aspirated and non-aspirated (embolized) particulates were collected, quantified and sized.

FIG. 10 shows experimental results using the interventional catheter assembly of the present invention in a laboratory model of obstructive heart disease. In the laboratory model, a 2 cm long lesion was simulated in a blood vessel-like structure and a liquid having a viscosity equivalent to blood was circulated. Aspirated and embolized particulate materials were collected as an interventional catheter systemced and rotated through the lesion. The size of the collected particulates was measured and the collected particulates were quantified. As shown in FIG. 10, particles of all sizes were effectively aspirated. FIG. 10 also shows that a large number of small particulates were aspirated and only a small number of very small particulates were not collected by the aspiration system and, in a clinical setting, may be embolized. The interventional catheter assembly of the present invention, constructed as described herein produced an aspiration efficiency of 97%.

The present invention has been described with reference to specific embodiments and figures. These specific embodiments should not be construed as limitations on the scope of the invention, but merely as illustrations of exemplary embodiments. It is further understood that many modifications, additions and substitutions may be made to the described interventional catheter and control system without departing from the broad scope of the present invention.

We claim:

1. An interventional catheter assembly comprising: a catheter system forming at least one passageway and being sized and configured for introduction to and navigation through a body lumen or cavity to a target site; an operating head positioned at or near a distal end of the catheter system and coupled to a drive shaft and a drive system for rotation; a guidewire brake operable to clamp a guidewire in a stationary position when engaged and to allow translation and/or rotation of the guidewire through the brake when released; a guidewire brake control system interrupt that prevents the drive system from being actuated when the guidewire brake is in a release position; and a selectable guidewire brake interrupt override control that, when actuated, permits an operator to translate and/or rotate the drive shall and operating head while the guidewire is simultaneously moved.

2. The interventional catheter assembly of claim 1, additionally comprising an aspiration lumen that communicates with a vacuum source during operation and provides aspiration of materials from the target site.

3. The interventional catheter assembly of claim 1, additionally comprising one or more material removal ports in proximity to the operating head.

4. The interventional catheter assembly of claim 1, additionally comprising an infusion lumen that communicates with an infusate source during operation and provides infusion of liquid to the target site.

5. The interventional catheter assembly of claim 1, additionally comprising control circuitry providing a delay between the time the drive system and an aspiration system are inactivated, such that the drive system may be inactivated immediately upon actuation of a switch, while the aspiration system may be inactivated after a delay period following actuation of the drive system.

6. The interventional catheter assembly of claim 1, wherein the operating head has advanceable, rotatable cutter surfaces at or near as distal end.

7. The interventional catheter assembly of claim 1, wherein the rotational output of the drive system is bidirectional.

8. The interventional catheter assembly of claim 1, additionally comprising a selection switch allowing an operator to change the direction of rotational output of the drive system.

9. The interventional catheter assembly of claim 1, wherein the drive system comprises a variable speed drive motor that delivers a constant voltage for any specified rotational output.

10. The interventional catheter assembly of claim 1, wherein the current delivered to the drive system is adjusted, under load conditions, if the voltage for any specified rotational output is insufficient to produce the specified rotational output.

11. The interventional catheter assembly of claim 1, provided as a sterile, disposable kit.

12. A method for operating an interventional catheter having an advanceable operating head positioned at or near a distal end of a catheter system sized for insertion into and navigation through a body lumen or cavity, comprising: inserting a flexible guidewire into and navigating the guidewire through a body lumen or cavity to a target site; inserting and navigating the advanceable operating head and a portion of the catheter system over the guidewire to the target site; actuating the operating head remotely and advancing it to separate and break down Undesired occlusive material at the target site; and withdrawing the operating head from the target site by simultaneously moving the guidewire and the operating head while rotating the operating head.

13. The method of claim 12, addition comprising clamping the guidewire in a position in which it is prevented from moving axially or rotatably after the guidewire is positioned at the target site.

14. The method of claim 12, wherein the body lumen or cavity is selected from the group consisting of: blood vessels and vascular cavities; gastrointestinal cavities; lumens or cavities in male and female reproductive organs, gas exchange cavities, a spinal canal, and nasal and sinus cavities.

15. The method of claim 12, additionally comprising aspirating the undesired occlusive material from the target site.

16. The method of claim 12, additionally comprising infusing liquid in proximity to the target site during actuation of the operating head.

17. The method of claim 12, additionally comprising sensing whether the guidewire is in a clamped or a released position.

18. The method of claim 17, additionally comprising providing a control system feature that permits rotation and advancement of the operating head when the guidewire is in a clamped condition and that prevents actuation of the operating head when the guidewire brake is in a released position.

19. A method for operating an interventional catheter having an advanceable, rotatable operating head positioned at or near a distal end of a catheter system sized for insertion into and navigation through a body lumen or cavity, comprising: inserting a flexible guidewire into and navigating the guidewire through a body lumen or cavity to a target site; inserting and navigating the advanceable operating head and a portion of the catheter system over the guidewire to the target site; clamping the guidewire prior to actuating the operating head and advancing the operating head over the guidewire at the target site while rotating the operating head; and withdrawing the operating head from the target site by translating and rotating the operating head while the guidewire is simultaneously moved.

* * * * *